United States Patent
Peterson

(10) Patent No.: US 6,187,712 B1
(45) Date of Patent: Feb. 13, 2001

(54) CATALYST COMPOSITION FOR THE POLYMERIZATION OF OLEFINS

(75) Inventor: Thomas Henry Peterson, Charleston, WV (US)

(73) Assignee: Univation Technologies, LLC

( * ) Notice: Under 35 U.S.C. 154(b), the term of this patent shall be extended for 0 days.

(21) Appl. No.: 09/154,460

(22) Filed: Sep. 16, 1998

(51) Int. Cl.$^7$ .............................. B01J 21/02; B01J 31/00; C08F 4/94; C08F 9/72
(52) U.S. Cl. ..................... 502/152; 502/202; 526/134; 526/170; 526/901
(58) Field of Search ................... 502/152, 202; 526/134, 170

(56) References Cited

U.S. PATENT DOCUMENTS

| | | | |
|---|---|---|---|
| 5,527,752 | 6/1996 | Reichle et al. | 502/123 |
| 5,585,508 | * 12/1996 | Kuber et al. | 502/152 |
| 5,776,851 | * 7/1998 | Kuber et al. | 502/152 |
| 6,030,918 | * 2/2000 | King et al. | 502/152 |
| 6,034,192 | * 3/2000 | Crowther et al. | 502/152 |
| 6,066,706 | * 2/2000 | Santi et al. | 526/134 |

FOREIGN PATENT DOCUMENTS

| | | | |
|---|---|---|---|
| 621010 | * 5/1961 | (CA) | 526/134 |
| 681141 | * 3/1964 | (CA) | 526/134 |
| 1 268 392 | * 5/1968 | (DE) | 526/134 |
| 820425 | * 9/1959 | (GB) | 526/134 |
| 835674 | * 5/1960 | (GB) | 526/134 |
| 882600 | * 5/1961 | (GB) | 526/134 |

OTHER PUBLICATIONS

Group 4 transition metal complex cations for olefin polymerization, Claudio Pellecchia et al., Makromol Chem., Rapid Commun, 12, 663–667 (1991).

Cationic Zirconium Benzyl Complexes as Catalysts for olefin polymerization: A comparison among dicyclopentadienyl, monocyclopentadienyl and Cp–Free Derivatives, Macromol, Symp. 89, 335–344 (1995).

Electron–deficient Group IV Metal Alkyl Cations, and the Synthesis of $Zr(CH_2Ph_3)BPh_3$ : a Fluxional Arene π–Complex of a d$^o$ Metal, Manfred Bochmann, et al., J. Chem. Soc., Chem. Comm. 1990 , pp. 1038–1039.

Base–Free Cationic Mono(cyclopentadietnyl)zirconium Complexes: Synthesis, Structural Characterization, and Catalytic Activity in Olefin Polymerization, Claudio Pellecchia, et al., Organometallics, 12, (1993) pp. 4473–4478.

Mono(η–cyclopentadietnyl)zirconium complexes: from coordination chemistry to enantioselective catalysis, Gerhard Erker, Journal of Organometallic Chemistry, 400 (1990) 185–203.

The formation and structures of the methyl–bridged complexes $Cp^*TiMe_2$ ($\mu$–Me)$B(C_6F_5)_3$ and[$Cp^*TiMe_2$ ($\mu$–Me)$TiMe_2$ $Cp^*$][$MeB(C_6F_5)_3$ ], Qinyan Wang, et al., Journal of Organometallic Chemistry 527 (1997) 7–14.

Facile α–C–H activation in 14–electron zirconium half sandwich compounds: evidence for a new catalyst deactivation pathway, Gerardo Jimenez Pindado, et al. Chem. Commun., 1997 pp. 609–610.

Polymerization of ethylene and propene in the presence of organometallic compounds of titanium and zirconium activated with tris(pentafluorophenyl)boron, Claudio Pellecchia, et al. Makromol Chem., Rapid Commun. 13, 277–281 (1992).

Non–metallocene group 4 organometallic complexes as catalysts for olefin polymerization: synthesis and catalytic activity of the cationic complex $[Zr(CH_2Ph_3]^{+[B(CH_2}Ph)(C_6F_5)_3]^-$, Pellecchia et al., J. Mol. Catal., 82 (1993) 57–65.

Alkyl and Hydride Derivatives of (Pentamethylcyclopentadienyl)zirconium (IV), Peter T. Wolczaski et al., Organometallics 1982, 1, 793–799.

Polymer Supported Zirconium Borohydride: a Stable, Efficient and Regenerable Reducing Agent, Bahman Tamami et al., J. Chem Soc., Chem. Commun. 1994, 1079.

Disproportionation of Cationic Zirconium Complexes: A Possible Pathway to the Deactivation of Catalytic Cationic Systems, Robert Choukroun, et al., Organometallics 1997, 16, 5517–5521.

Cyclic Hydroborate Complexes of Metallocenes. 1. Organodiborate Ring Transformations Promoted by Zirconocene and Hafnocene Dichlorides. Syntheses and Structures of Zirconocene and Hafnocene Boracyclopentance Derivatives, Glenn T. Jordan, et al. Inorg. Chem 1997, 36, 5597–5602.

Catalysts Prepared By the Interaction of Transition Metal Tetrahydroborates with Oxide Supports: Synthesis of Surface Ti, Zr, Hf Hydrides and Their Catalytic Properties in Ethylene Polymerization, G.A. Nesterov et al. Journal of Molecular Catalysis, 36 (1986) 253–269.

The Reactions of Lewis Bases with Tetrahydroborate Derivatives of the Group IVa Elements. The Preparation of New Zirconium Hydride Species, B.D. James et al. J. Chem. Soc. A. 1966, 182–184.

Preparation of Titanium Pentamethylcyclopentadienyl Trialkyls and Crystal Structure of Tribenzylpentamethylcyclopentadienyltitanium, showing Some Evidence of a $CH_2$ Ti Interaction, Miguel Mena, et al. J. Chem Soc., Chem., Commun., (1986) 1118–1119.

* cited by examiner

Primary Examiner—Mark L. Bell
Assistant Examiner—J. Pasterczyk
(74) Attorney, Agent, or Firm—Lisa Kimes Jones; Jaimes Sher

(57) ABSTRACT

A catalyst composition for the polymerization of olefins is provided. The catalyst composition comprises a mono- or biscycloalkadienyl catalyst precursor comprising at least one protected hydride ligand or protected hydrocarbyl ligand bound to a metal atom plus a cocatalyst. The protected hydride ligand is preferably a borohydride ligand.

15 Claims, No Drawings

CATALYST COMPOSITION FOR THE POLYMERIZATION OF OLEFINS

The present invention relates to a catalyst composition useful for the polymerization of olefins. The catalyst composition comprises a mono- or biscycloalkadienyl catalyst precursor comprising at least one protected hydride or protected hydrocarbyl ligand bound to a metal atom and a cocatalyst.

BACKGROUND OF THE INVENTION

A variety of catalyst compositions containing single site catalyst precursors have been shown to be highly useful in the preparation of polyolefins, producing relatively homogeneous copolymers at good polymerization rates and allowing one to tailor the properties of the finished polymer closely. In contrast to traditional Ziegler-Natta catalyst compositions, single site catalyst compositions comprise catalytic compounds in which each catalyst composition molecule contains one or only a few polymerization sites.

The most well known category of single site catalyst precursors is metallocenes of the general formula $Cp_2MX_2$ wherein Cp is a cycloalkadienyl ligand, typically cyclopentadienyl or indenyl, M is a metal, usually from Group 4, and X is a halogen or alkyl group.

Other types of single site catalyst precursors have more recently been reported. Wolczanski et al., *Organometallics*, 1:793 (1982) describes the synthesis of $Cp^*Zr(BH_4)_3$ and a related dimer, $[Cp^*Zr(BH_4)H(\mu-H)]_2$, wherein $Cp^*$ is pentamethylcyclopentadienyl. The authors state on page 794, the dimer "appears to polymerize ethylene; however, the low rate of oligomerization may indicate trace impurities are responsible."

The present invention revolves around the discovery that single site catalyst precursors comprising at least one protected hydride or protected hydrocarbyl ligand bound to a metal atom combined with a cocatalyst are particularly effective for the polymerization of olefins. Protected hydride or hydrocarbyl ligands are quite stable when attached to the metal of ligated catalyst precursor. In contrast to the findings of Wolczanski et al., this unique combination of precursor and cocatalyst provides an extremely active catalyst composition.

SUMMARY OF THE INVENTION

The invention provides a catalyst composition for the polymerization of olefins comprising: a) a catalyst precursor of the formula $L_xM^{n+}(A)_y[R_zZ]_{(n-x-y)}$, wherein each L is a cycloalkadienyl ligand; M is an element selected from Groups 3 to 10 and the Lanthanides; each A is an anionic group; each R is carbon or hydrogen; each Z is a protecting moiety containing an element from Group 13 through which Z is bridged to M via R; x is 0, 1 or 2; n is the valence of M; y is an integer from 0 to 7; and Z is an integer from 1 to 4 and b) a cocatalyst.

The invention also provides a process for preparing the above catalyst precursor, as well as processes for the polymerization of olefins which comprise contacting olefins under polymerization conditions with the above catalyst composition.

DETAILED DESCRIPTION OF THE INVENTION

Olefin polymers that may be produced according to the invention include, but are not limited to, ethylene homopolymers, homopolymers of linear or branched higher alpha-olefins containing 3 to about 20 carbon atoms, and interpolymers of ethylene and such higher alpha-olefins, with densities ranging from about 0.86 to about 0.96. Suitable higher alpha-olefins include, for example, propylene, 1-butene, 1-pentene, 1-hexene, 4-methyl-1-pentene, 1-octene, and 3,5,5-trimethyl-1-hexene. Olefin polymers according to the invention may also be based on or contain conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene, norbornadiene and the like. Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well. Specific olefin polymers that may be made according to the invention include, for example, polyethylene, polypropylene, ethylene/propylene rubbers (EPR's), ethylene/propylene/diene terpolymers (EPDM's), polybutadiene, polyisoprene and the like.

The catalyst precursor has the formula $L_xM^{n+}(A)_y[R_zZ]_{(n-x-y)}$. Each L is an unsubstituted or substituted cycloalkadienyl ligand, i.e., cyclopentadienyl, indenyl, or fluorenyl groups optionally substituted with one or more hydrocarbyl groups containing 1 to 20 carbon atoms. Examples of L include cyclopentadienyl, indenyl, fluorenyl, methylcyclopentadienyl, 1,2-dimethylcyclopentadienyl, 1,3-dimethylcyclopentadienyl, 2,3,4,5-tetramethylcyclopentadienyl, pentamethylcyclopentadienyl, trimethylsilylcyclopentadienyl, phenylcyclopentadienyl, indenyl, fluorenyl, trimethylsilylindenyl, 2-methylindenyl, 2-arylindenyl, and trimethylsilylfluorenyl. Preferably, L is selected from methylcyclopentadienyl, 1,3-dimethylcyclopentadienyl, indenyl, fluorenyl, and 2-arylindenyl. More preferably, L is selected from methylcyclopentadienyl, 1,3-dimethylcyclopentadienyl, indenyl, and fluorenyl. Most preferably, L is methylcyclopentadienyl.

M is an element selected from Groups 3 to 10 and the Lanthanides. Preferably, M is selected from Groups 3, 4, 5, 6 and the Lanthanides. More preferably, M is a Group 4 element. Zirconium in particular is preferred.

Each A is an anion, and may be multifunctional. Preferably, each A is selected from hydrogen, an aryl, alkyl, alkenyl, alkylaryl, or arylalkyl radical having 1–20 carbon atoms, a halogen, chalcogen or pnictogen. More preferably, each A is selected from hydrogen, aryl or alkyl. Most preferably, A is hydrogen.

The group $[R_zZ]$ is a protected hydride or hydrocarbyl group wherein Z is linked to M via R. Preferably, each R is hydrogen or carbon. Most preferably, R is hydrogen. Each Z is a protecting moiety containing an element from Group 13 through which the group Z is connected to M via R. More preferably, each Z is boron or aluminum. Most preferably, each Z is boron. In a preferred embodiment of the invention, the $[R_zZ]$ group is a borohydride group of the formula $[BH_4]$.

In the above formula, x is 1 or 2; n is the valence of M; and y is an integer from 0 to 7 and Z is an integer from 1 to 4.

In a preferred embodiment of the invention, the catalyst precursor has the formula: $L_xM^{n+}(BH_4)_{n-x}$ wherein L, M, n have the meanings above, and x' is 1 or 2.

More preferably, the catalyst precursor has one of the formulas:

(1)
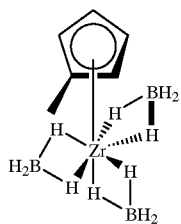

(2)
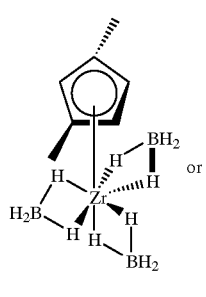
or (3)
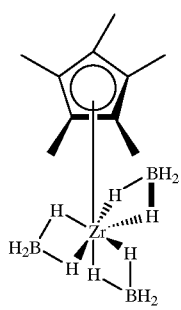

The catalyst precursor may be made by any means, and the invention is not limited thereby. For example, a preferred method of making the catalyst precursor is by reaction of a compound containing at least two protected hydride or hydrocarbyl ligands bound to a metal atom with an anionic donor. In this reaction the anion of the anionic donor is substituted for one of the protected hydride or hydrocarbyl ligands to form the catalyst precursor.

The compound containing at least two protected hydride or hydrocarbyl ligands bound to a metal atom is preferably a homoleptic metal ligand complex, more preferably a homoleptic Group 4, 5, or 6 metal ligand complex. Most preferably, the compound containing at least two protected hydride or hydrocarbyl ligands bound to a metal atom is a homoleptic Group 4 metal ligand complex, such as zirconium tetraborohydride.

The anionic donor may be an atom or group of atoms capable of donating an anion to the compound containing at least two protected hydride or hydrocarbyl ligands bound to a metal atom. Examples include anionic fragments of oxygen-, nitrogen-, sulfur- and phosphorus-containing compounds such as alkoxides, amides, thiolates, or phosphides as well as hydrocarbyl, or aryl groups bearing a negative charge. Additionally, the anionic donor may be a single atom as in the case of the halides or a hydride donor. Alternatively, the anionic donor may contain an L ligand described above. A preferred class of anionic donor is salts of cycloalkadienyl ligands, more preferably alkaline or alkaline earth metal salts of cycloalkadienyl ligands. Examples of alkaline metal and alkaline earth metal salts of cycloalkadienyl ligands include cyclopentadienyllithium and its sodium and potassium congeners, indenyllithium and its sodium and potassium congeners, and fluorenyllithium and its sodium and potassium congeners. Other examples of alkaline metal and alkaline earth metal salts of cycloalkadienyl ligands include bis(cyclopentadienyl)magnesium and bis(cyclopentadienyl)calcium. Salts of substituted cycloalkadienyl ligands may be used as well.

For example, the preferred catalyst precursors of formulas 1 and 2 above may be made according to this method by reaction of the homoleptic borohydride complex $Zr(BH_4)_4$ with a cycloalkadienyl salt:

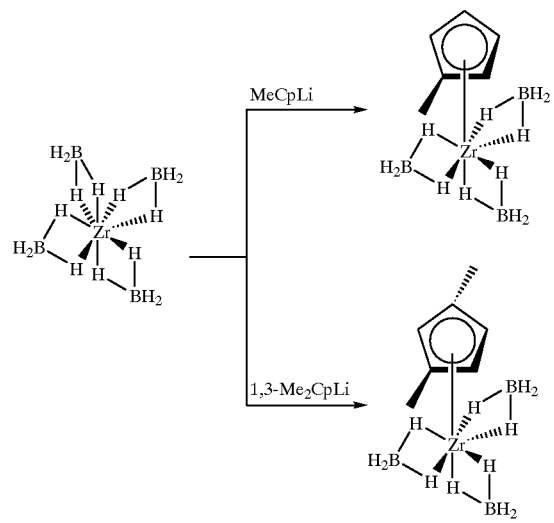

The cocatalyst is one that is capable of abstracting an A or [RZ] group from the catalyst precursor. Any cocatalysts useful with single site catalyst precursors may be used. Examples of such cocatalysts include salts, such as carbenium or ammonium salts, of borates and aluminates, boranes, aluminum alkyls, and alumoxanes. Preferably, the cocatalyst is a salt comprising a cation selected from triphenylcarbenium, dimethylanilinium, and trialkylammonium and an anion selected from borate and aluminate. More preferably, the cocatalyst is a borate of the formula $BR''_4^-$, wherein R" is a strong-electron withdrawing moiety such as perfluoroaryl, perfluoroalkyl or perfluoroalkyl-substituted moieties. Most preferably the cocatalyst is triphenylcarbenium tetrakis(pentafluorophenyl)borate.

The catalyst composition may be impregnated onto a solid, inert support, in liquid form such as a solution or dispersion, spray dried, in the form of a prepolymer, or formed in-situ during polymerization. Particularly preferred among these is a catalyst composition that is spray dried as described in U.S. Pat. No. 5,648,310 or in liquid form as described in U.S. Pat. No. 5,317,036. For example, the catalyst composition may be introduced into the reaction zone in unsupported, liquid form as described in U.S. Pat. No. 5,317,036. As used herein, "unsupported, liquid form" includes liquid catalyst precursor, liquid cocatalyst, solution(s) or dispersions thereof in the same or different solvent(s), and combinations thereof. Unsupported, liquid form catalyst compositions have a number of practical benefits. Unsupported catalyst compositions avoid the costs associated with support material and its preparation, and provide for the realization of a very high catalyst surface area to volume ratio. Furthermore, unsupported catalyst compositions produce polymers having a much lower residual ash content than polymers produced using supported catalyst compositions.

In the case of a supported catalyst composition, the catalyst composition may be impregnated in or deposited on the surface of an inert substrate such as silica, carbon black, polyethylene, polycarbonate porous crosslinked polystyrene, porous crosslinked polypropylene, alumina, thoria, zirconia, or magnesium halide (e.g., magnesium dichloride), such that the catalyst composition is between 0.1 and 90 percent by weight of the total weight of the catalyst composition and the support.

The catalyst composition may be used for the polymerization of olefins by any suspension, solution, slurry, or gas phase process, using known equipment and reaction conditions, and is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000 psi, preferably 50 to 400 psi, most preferably 100 to 300 psi, and temperatures in the range of 30 to 130° C., preferably 65 to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,528,790 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum.

Conventional adjuvants may be included in the process, provided they do not interfere with the operation of the catalyst composition in forming the desired polyolefin. Hydrogen or a metal or non-metal hydride, e.g., a silyl hydride, may be used as a chain transfer agent in the process. Hydrogen may be used in amounts up to about 10 moles of hydrogen per mole of total monomer feed.

Aluminum alkyls such as trimethylaluminum, triethylaluminum, or triisobutylaluminum may also be added to the process, or to the catalyst composition directly.

The following examples further illustrate the invention.

EXAMPLES

Polymerization catalyst precursors and activated catalysts are moisture- and air sensitive materials and all manipulations described below were performed in a glove box containing prepurified nitrogen or by using standard Schlenk techniques.

Triphenylcarbenium tetrakis(pentafluorophenyl)borate used was purchased from Akzo Nobel or Boulder Scientific. $(C_5Me_5)Zr(BH_4)_3$ was prepared according to the procedure of Wolczanski and Bercaw (vide supra). All other reagents and solvents were purchased from Aldrich Chemical company unless otherwise noted.

Preparation of Methylcyclopentadienyl tris(tetrahydroborato)zirconium.

In an oven-dried 250 mL Schlenk flask was placed lithium borohydride (1.00 g, 46 mmol) and zirconium tetrachloride (2.67 g, 11.46 mmol). The flask was evacuated on a vacuum manifold and 200 mL of dry diethyl ether was added to the reaction flask via vacuum transfer. After warming to room temperature, the reaction was allowed to stir for a period of 60 minutes. In a second Schlenk flask was placed 750 mg (8.73 mmol) of solid methylcyclopentadienyllithium. The flask was evacuated and cooled in a liquid nitrogen bath and the volatile contents of the first reaction flask were condensed via vacuum transfer in the second flask. After stirring for a period of 90 minutes, the volatile materials were removed in vacuo and the crude product was extracted with three 10 mL portions of hexanes. After filtration through a Celite pad, the solvent was removed under vacuum and the residue was recrystallized from 10 mL of hexanes at −35° C. to afford 1.40 g of pure methylcyclopentadienyl tris(tetrahydroborato) zirconium in 75% yield from a single crop.

Slurry-Phase Ethylene-1-Hexene Copolymerization by $(C_5Me_5)Zr(BH_4)_3$/Triphenylcarbenium tetrakis(pentafluorotphenyl)borate.

Into a 1 L stirred autoclave reactor under a nitrogen purge and maintained at temperature of 55° C. was placed 600 mL of dry hexane. 1-Hexene (43 mL) and triisobutylaluminum (100 µL of 1 M solution in hexane, 100 µmol) were added via syringe. After stirring for approximately 10 minutes, the reactor was pressurized to 85 psi with ethylene and was heated to 75 ° C.

A catalyst solution was prepared by dissolving a solid mixture of $(C_5Me_5)Zr(BH_4)_3$ (5.0 mg, 11.9 µmol) and triphenylcarbenium tetrakis(pentafluorophenyl)borate (37 mg, 40 µmol) in toluene (5 mL). The polymerization was carried out by injecting a 0.200 mL aliquot of activated catalyst solution into the reactor with maintenance of the set temperature and pressure for a period of 30 minutes. Polymerization activities were calculated as g polymer mmol $Zr^{-1}$ $h^{-1}$ (100 p.s.i. ethylene)$^{-1}$. The results are shown in Table 1 below, Examples 1 and 2.

Slurry-Phase Ethylene-1-Hexene Copolymerization by $(MeCp)Zr(BH_4)_3$/Triphenylcarbenium tetrakis (pentafluorophenyl)borate.

Into a 1 L stirred autoclave reactor under a nitrogen purge and maintained at temperature of 55 ° C. was placed 600 mL of dry hexane. 1-Hexene (43 mL) and triisobutylaluminum (200 μL of 1 M solution in hexane, 100 μmol)were added via syringe. After stirring for approximately 10 minutes, the reactor was pressurized to 85 p.s.i with ethylene and was heated to 75 ° C.

A catalyst solution was prepared by dissolving a solid mixture of $(MeCp)Zr(BH_4)_3$ (5.0 mg, 23.2 μmol) and triphenylcarbenium tetrakis(pentafluorophenyl)borate (63.6 mg, 69 μmol) in toluene (12 mL) and triisobutylaluminum (26 μL). The polymerization was carried out by injecting a 0.490 mL aliquot of activated catalyst solution into the reactor with maintenance of the set temperature and pressure for a period of 30 minutes. Alternatively, the amount of catalyst may be adjusted by varying the solution volume involved in the preparation or the volume of catalyst solution injected into the reactor. Polymerization activities were calculated as g polymer mmol $Zr^{-1}$ $h^{-1}$ (100 p.s.i. ethylene)$^{-1}$. The results are shown in Table 1 below, Examples 3–5.

TABLE 1

| Example | Catalyst | Co-catalyst | μmol cat | g PE | Activity |
|---|---|---|---|---|---|
| 1 | $(C_5Me_5)Zr(BH_4)_3$ | $[CPh_3][B(C_6F_5)_4]$ | 0.75 | 6.8 | 20915 |
| 2 | $(C_5Me_5)Zr(BH_4)_3$ | $[CPh_3][B(C_6F_5)_4]$ | 0.75 | 5.6 | 17224 |
| 3 | $(MeCp)Zr(BH_4)_3$ | $[CPh_3][B(C_6F_5)_4]$ | 0.95 | 58.6 | 142293 |
| 4 | $(MeCp)Zr(BH_4)_3$ | $[CPh_3][B(C_6F_5)_4]$ | 0.50 | 59.5 | 276724 |
| 5 | $(MeCp)Zr(BH_4)_3$ | $[CPh_3][B(C_6F_5)_4]$ | 0.23 | 23.2 | 232185 |

I claim:

1. A catalyst composition for the polymerization of olefins comprising:

a) a catalyst precursor of the formula $L_xM^{n+}(A)_y[R_zZ]_{(n-x-y)}$, wherein each L is a cycloalkadienyl ligand; M is an element selected from Groups 3 to 6 and the Lanthanides; each A Is an anionic group; each R is a carbon containing group or hydrogen; each Z is boron or aluminum and is bridged to M via P; x is 1 or 2; n is the valence of M; and y is an integer from 0 to 7 ; z is an integer from 1 to 4; and (n-x-y) is a positive integer; and b) a cocatalyst.

2. The catalyst composition of claim 1, wherein the catalyst precursor has the formula $L_xM^{n+}(BH_4)_{n-x}$ wherein each L is a cycloalkadienyl ligand; M is an element selected from Groups 3 to 6 and the Lanthanides; n is the valence of M; and x is 1 or 2.

3. The catalyst composition of claim 1, wherein the catalyst precursor has a formula selected from the group consisting of:

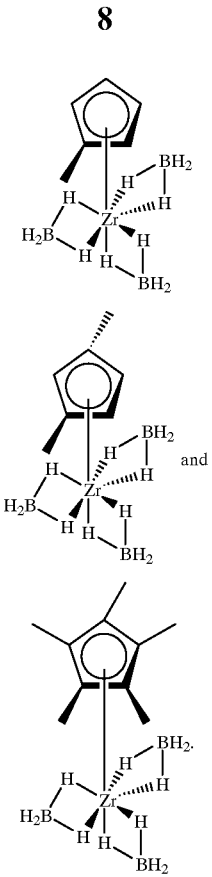

4. The catalyst composition of claim 1, wherein the cocatalyst is a borate of the formula $BR''_4^-$, wherein R'' is selected from the group consisting of perfluoroaryl, perfluoroalkyl, and perfluoroalkyl-substituted moieties.

5. The catalyst composition of claim 1, wherein the cocatalyst is triphenylcarbenium tetrakis (pentafluorophenyl)borate.

6. The catalyst composition of claim 1 in liquid form.

7. The catalyst composition of claim 1 further comprising an inert support.

8. A process for the polymerization of olefins, which comprises contacting olefins under polymerization conditions with a catalyst composition comprising:

a) a catalyst precursor of the formula $L_xM^{n+}(A)_y[R_zZ]_{(n-x-y)}$ ; wherein each L is a cycloalkadienyl ligand; M is an element selected from Groups 3 to 6 and the Lanthanides; each A is an anionic group; each R is carbon containing group or hydrogen; each Z is boron or aluminum and is bridged to M via R; x is 1 or 2; n is the valence of M; y is an integer from 0 to 7; z is an integer from 1 to 4; and (n-x-y) is a positive integer; and b) a cocatalyst.

9. The process of claim 8, wherein the catalyst precursor has the formula: $L_xM^{n+}(BH_4)_{n-x}$ wherein each L is a cycloalkadienyl ligand; M is an element selected from Groups 3 to 6 and the Lanthanides; n is the valence of M; and x is 1 or 2.

10. The process of claim 8 wherein the catalyst precursor has a formula selected from the group consisting of:

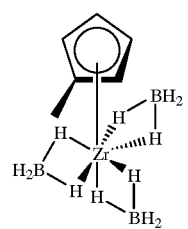

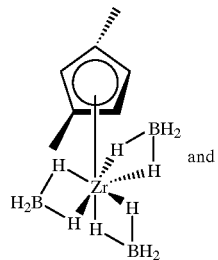 and

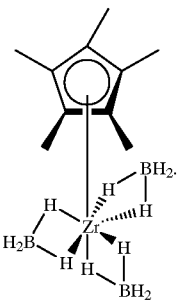

11. The process of claim 8, wherein the cocatalyst is a borate of the formula $BR''_4{}^-$, wherein $R''$ is selected from the group consisting of perfluoroaryl, perfluoroalkyl, and perfluoroalkyl-substituted moieties.

12. The process of claim 8, wherein the cocatalyst is triphenylcarbenium tetrakis(pentafluorophenyl)borate.

13. The process of claim 8, conducted in the gas phase.

14. The process of claim 8, wherein the catalyst composition is in liquid form.

15. The process of claim 8, wherein the catalyst composition further comprises an inert support.

* * * * *